(12) United States Patent
Morgan et al.

(10) Patent No.: US 11,504,054 B2
(45) Date of Patent: Nov. 22, 2022

(54) INTRA-UTERINE MONITORING SYSTEM

(71) Applicant: University of Southampton, Southampton (GB)

(72) Inventors: Hywel Morgan, Wiltshire (GB); Ying Cheong, Southampton (GB); Nick Macklon, London (GB); Shilong Lu, Southampton (GB)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 390 days.

(21) Appl. No.: 16/489,219

(22) PCT Filed: Mar. 7, 2017

(86) PCT No.: PCT/GB2017/050609
§ 371 (c)(1),
(2) Date: Aug. 27, 2019

(87) PCT Pub. No.: WO2018/162868
PCT Pub. Date: Sep. 13, 2018

(65) Prior Publication Data
US 2020/0060607 A1     Feb. 27, 2020

(51) Int. Cl.
*A61B 5/00*       (2006.01)
*A61B 5/01*       (2006.01)
(Continued)

(52) U.S. Cl.
CPC ............ *A61B 5/4325* (2013.01); *A61B 5/002* (2013.01); *A61B 5/0002* (2013.01);
(Continued)

(58) Field of Classification Search
CPC ..... A61B 5/4325; A61B 5/0031; A61B 5/035; A61B 5/6875; A61B 2560/0219
See application file for complete search history.

(56) References Cited

U.S. PATENT DOCUMENTS

| 4,616,640 A | 10/1986 | Kaali et al. |
| 4,676,254 A | 6/1987 | Frohn |

(Continued)

FOREIGN PATENT DOCUMENTS

| CN | 101248987 A | 8/2008 |
| CN | 103079632 A | 5/2013 |

(Continued)

OTHER PUBLICATIONS

Japanese Notice of Reasons for Rejection, Application No. 2019-546889, dated Jan. 6, 2021, 4 pages.

(Continued)

*Primary Examiner* — Daniel L Cerioni
*Assistant Examiner* — Raymond P Dulman
(74) *Attorney, Agent, or Firm* — Armstrong Teasdale LLP

(57) ABSTRACT

An intra-uterine monitoring system is described. The system comprises an implantable sensor device, shaped and dimensioned for implantation in a uterus for measuring conditions within the uterus to generate sensor data, and a wearable receiver device, for wirelessly receiving the sensor data generated by the implantable sensor device. In this way, real-time, in-vivo monitoring of the intra-uterine environment can be performed. The implantable sensor device can be kept small and simple, requiring only the mechanical and electronic structures necessary to take sensor measurements and transmit those to the receiver device. By making the receiver device wearable, it can be kept in relatively close proximity to the implantable sensor device on a long-term basis, making regular monitoring viable.

22 Claims, 12 Drawing Sheets

(51) Int. Cl.
  *A61B 5/03* (2006.01)
  *A61B 5/0538* (2021.01)
  *A61B 5/145* (2006.01)
  *H04Q 9/00* (2006.01)
  *A61B 5/07* (2006.01)

(52) U.S. Cl.
  CPC .............. *A61B 5/0031* (2013.01); *A61B 5/01* (2013.01); *A61B 5/035* (2013.01); *A61B 5/0538* (2013.01); *A61B 5/07* (2013.01); *A61B 5/14539* (2013.01); *A61B 5/14542* (2013.01); *A61B 5/6847* (2013.01); *H04Q 9/00* (2013.01); *A61B 5/6875* (2013.01); *A61B 2560/0214* (2013.01); *A61B 2560/0219* (2013.01); *A61B 2560/04* (2013.01); *H04Q 2209/40* (2013.01); *H04Q 2209/88* (2013.01)

(56) References Cited

U.S. PATENT DOCUMENTS

| | | | |
|---|---|---|---|
| 5,184,619 A | | 2/1993 | Austin |
| 5,373,852 A | | 12/1994 | Harrison et al. |
| 5,377,673 A | | 1/1995 | Van Dell |
| 5,431,171 A | * | 7/1995 | Harrison ............... A61B 5/0011 600/511 |
| 7,044,911 B2 | | 5/2006 | Drinan et al. |
| 8,290,556 B2 | * | 10/2012 | Rabinovitz .......... A61B 5/1459 600/302 |
| 8,292,808 B2 | | 10/2012 | Miller et al. |
| 8,401,659 B2 | | 3/2013 | Von Arx et al. |
| 8,496,597 B2 | | 7/2013 | James et al. |
| 8,540,644 B2 | | 9/2013 | Husheer |
| 8,591,403 B2 | | 11/2013 | Yoshida et al. |
| 8,656,916 B2 | | 2/2014 | Stukanov |
| 8,715,204 B2 | | 5/2014 | Webster et al. |
| 2003/0004403 A1 | | 1/2003 | Drinan et al. |
| 2003/0014091 A1 | | 1/2003 | Rastegar et al. |
| 2004/0174258 A1 | * | 9/2004 | Edelstein .................. A61B 5/00 340/539.13 |
| 2005/0004473 A1 | * | 1/2005 | Fujita ........................ A61B 5/07 600/300 |
| 2005/0143623 A1 | | 6/2005 | Kojima |
| 2008/0021341 A1 | * | 1/2008 | Harris ................. A61N 1/37229 600/544 |
| 2010/0081895 A1 | | 4/2010 | Zand |
| 2016/0030010 A1 | | 2/2016 | Johnson et al. |
| 2017/0095667 A1 | * | 4/2017 | Yakovlev ............. A61B 5/1118 |
| 2017/0272699 A1 | * | 9/2017 | Stopek ................. A61B 5/0011 |

FOREIGN PATENT DOCUMENTS

| | | |
|---|---|---|
| CN | 104758123 A | 7/2015 |
| CN | 106073798 A | 11/2016 |
| EP | 0476730 A1 | 3/1992 |
| JP | 2004121733 A | 4/2004 |
| JP | 2005103147 A | 4/2005 |
| JP | 2006034678 A | 2/2006 |
| JP | 2016520340 A | 7/2016 |
| WO | 2009109966 A1 | 9/2009 |
| WO | 2011039680 A1 | 4/2011 |
| WO | 2011094075 A2 | 8/2011 |
| WO | 20140144070 A1 | 9/2014 |

OTHER PUBLICATIONS

Examination Report for Indian Patent Application No. 201917035683, 5 pages, Jan. 1, 2022.
Mundt C et al: "Advanced Sensor Systems for Improved Labor and Fetal Monitoring", Technical Paper of ISA, Instrumental Society of America, vol. 2, No. Part 02, Jan. 1, 1998, pp. 79-89, XP000875217, ISSN: 1054-0032.
International Search Report and Written Opinion issued for PCT/GB2017/050609, dated Nov. 14, 2017, 14 pages.
European Examination Report, Application No. 17718111.2-, dated Sep. 29, 2021, 5 pages.

* cited by examiner (c)

(d)

INTRA-UTERINE MONITORING SYSTEM

CROSS-REFERENCE TO RELATED APPLICATION

This application is the 35 U.S.C. § 371 national stage of PCT/GB2017/050609, filed Mar. 7, 2017, which is incorporated herein by reference in its entirety.

TECHNICAL FIELD

The present invention relates to an intra-uterine monitoring system. Embodiments of the present invention relate to a system for long-term, real-time, in-vivo measurement of biophysical parameters in a human uterus.

BACKGROUND

More than 30% of all human conceptions do not advance beyond 20 weeks of gestation. One in six couples suffer from infertility, and in around 25% of couples no clear reason is identified. Even after assistance from artificial reproductive technologies, take home baby rates have altered little in the last five to ten years. This may reflect the lack of pathophysiologic understanding and clinically relevant diagnostic approaches for interrogating uterine functions. An interaction between the intra-uterine environment (biophysical parameters, such as temperature, dissolved oxygen concentration and pH) and reproductive health is likely, but very little is known about the biophysical characteristics of the uterus and how they alter through the menstrual cycle. The available data is mostly derived from snapshot technology and wired sensor probes, both of which do not enable real-time long-term in-vivo monitoring.

The present invention is intended to address certain of these limitations.

SUMMARY OF THE INVENTION

According to an aspect of the present invention, there is provided an intra-uterine monitoring system, comprising:
  an implantable sensor device, shaped and dimensioned for implantation in a uterus for measuring conditions within the uterus to generate sensor data; and
  a wearable receiver device, for wirelessly receiving the sensor data generated by the implantable sensor device.

In this way, real-time, in-vivo monitoring of the intra-uterine environment can be performed. The implantable sensor device can be kept small and simple, requiring only the mechanical and electronic structures necessary to take sensor measurements and transmit those to the receiver device. By making the receiver device wearable, it can be kept in relatively close proximity to the implantable sensor device on a long-term basis, making regular monitoring viable.

Preferably, the wearable receiver device is operable to wirelessly charge the implantable sensor device. In this way, a battery is not required in the implantable sensor device, enabling it to be made smaller, and avoiding potential problems associated with battery leakage within the uterus. The wireless charging may be conducted using electromagnetic field coupling wireless energy transfer. The wearable receiver device may comprise an antenna, transceiver circuitry and a power source, and the implantable sensor device may comprise an antenna, a charging circuit and a controller. The wearable receiver device may be operable to transmit electrical power from the antenna of the wearable receiver device to the antenna of the implantable sensor device via electromagnetic coupling. The electrical power is used by the charging circuit to store electrical power for operating the sensors of the implantable sensor device and for transmitting sensor data to the wearable receiver device. The implantable sensor device may comprise a capacitor, and the charging circuit may store the electrical power by charging the capacitor. The power source may be a rechargeable battery.

The wearable receiver device may provide electrical power to the implantable sensor device in a plurality of charging periods over a single cycle of operation. As a result, the capacitor or other electrical storage device may be kept small, since it need only be large enough (in electrical terms) to store sufficient electrical charge to execute a portion of an operational cycle. The plurality of charging periods may comprise a first charging period for providing the implantable sensor device with electrical power to support the operation of the sensors in acquiring sensor data and a second charging period for providing the implantable sensor device with electrical power to support the transmission of the acquired sensor data to the wearable receiver device. The plurality of charging periods may also comprise a third charging period, carried out before the first charging period, for providing the implantable sensor device with electrical power to support a booting procedure. The third charging period may comprise an initial charging operation and a variable length multi-charging operation.

The wearable receiver device may comprise a plurality of antennae which are working cooperatively, each antenna being operable to wirelessly charge and receive data from the implantable sensor device. It will be appreciated that power transfer and data transfer between two antennae is highly dependent on the distance, relative orientation, and physical obstructions between them. By providing a plurality of antennae at different positions and/or orientations of the wearable receiver device, it is possible to increase the reliability of being able to charge up and receive data from the implantable sensor device. The wearable receiver device may comprise a controller, the controller being operable to sequentially charge the implantable sensor device using a plurality of the antennae. The controller may be operable to identify which of the plurality of antennae are able to wirelessly detect the implantable sensor device prior to a charging operation, and to sequentially charge the implantable sensor device using each identified antenna. The controller may be operable to attempt to obtain the sensor data using one of the identified antenna, and if the attempt fails then attempt to obtain the sensor data using one or more other of the identified sensors.

The implantable sensor device may comprise one or more of a temperature sensor, a pH sensor and a dissolved oxygen sensor. These sensors, which may be miniaturised electrochemical sensors integrated into the sensor device, are particularly appropriate for human fertility analysis applications. Other biophysical parameter sensors could also be used, for example electrical conductivity or pressure sensors could be provided. In some cases, multiple sensors of the same type (for example temperature sensors) may be provided at different locations on the implantable sensor device, for example in the form of a sensor array. This enables separate measurements to be made at different regions within the uterus. For example, a first temperature sensor could be provided at one end of the implantable sensor device, proximate the cervix, while a second temperature sensor could be provided at the other end of the implantable sensor device, further into the uterus. In this way, a temperature distribution, or gradient, can be inferred.

The implantable sensor device may comprise a body and one or more arms projecting laterally from the body to secure the sensor within the uterus. This should increase the likelihood of the device remaining in place throughout the desired implantation period. The implantable sensor device may comprise a pair of arms positioned at or proximate one end of the body and extending generally away from each other. These structures have been found to provide stable positioning of the implantable sensor device within a uterus.

The wearable receiver device may be a belt to be worn around the waist of a user. Alternatively, the wearable receiver device may be a sanitary pad. It will be appreciated that the device may take alternative forms, for example underwear. As a result, the system provides negligible interference to a users' daily life.

The wearable receiver device may comprise a transmitter for wirelessly transmitting received sensor data to an external device. The external device may be a portable electronic device (such as a mobile telephone, a tablet, or a dedicated handset) or a computer. The external device may be a remote server, or a database for building up a library of sensor data.

Generally, embodiments of the present invention provide a multi-parameter in-vivo sensing platform for long-term capture of critical biophysical parameters in the uterus in real-time. Such embodiments include a miniaturised wireless and battery-less implantable sensor, a wearable receiver with various antennas, and custom software. The implantable sensor should preferably be well packaged and secure for safety reasons, given its intended insertion into the uterus of a live subject.

Conventional approaches for uterus internal environment, endometrium evaluation involve sampling first and analysis afterwards. These approached are limited in sensitivity and accuracy, and are only suitable to certain biological parameters. Currently, most available data is captured by sensor probes wired to an equipment or handheld machine, which can only perform "snapshot" measurements for a short period of time. In contrast, the presently proposed implantable intra-uterine sensing system may achieve long-term, real-time in-vivo measurement for human fertility research, intra-uterine environment evaluation and endometrium evaluation. The miniaturised wireless and battery-less implantable sensor for intra-uterine measurement can be made size-suitable for the uterus cavity and properly positioned to remain in place for a relatively long period of time (weeks or months), permitting continuous monitoring during this time. The sensor is able to measure the biophysical/physiological properties within a human body (in-vivo) in the required environment, on a real-time or near real-time basis, and minimises the possibility of erroneous measurement being made, to improve sensitivity, accuracy and response time.

In an alternative aspect, the invention provides an intra-uterine monitoring system, comprising:
an implantable sensor device, shaped and dimensioned for implantation in a uterus for measuring conditions within the uterus to generate sensor data; and
an external receiver device, for wirelessly receiving the sensor data generated by the implantable sensor device. The external receiver device may be wearable, as defined above, or may be embedded in an item of furniture such as a chair or a bed, permitting the collection of the sensor data while the subject being monitored is sitting or lying down. It will be appreciated that, in some implementations only the antenna of the receiver device may be embedded in the item of furniture, with the remainder of the receiver device being removably detachable from the antenna for example. As with a wearable receiver device, the external receiver device embedded in an item of furniture may wirelessly charge the implantable sensor device. Generally, the optional and preferred features of the invention described above in relation to a wearable receiver device are equally applicable where the external receiver device forms part of an item of furniture.

A further aspect of the present invention provides an implantable sensor device, shaped and dimensioned for implantation in a uterus for measuring conditions within the uterus to generate sensor data, the implantable sensor device being operable to wirelessly communicate the sensor data to a wearable receiver device. A further aspect of the present invention provides a wearable receiver device, for wirelessly receiving sensor data generated by an implantable sensor device implanted in a uterus to measure conditions within the uterus.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Figure 1:
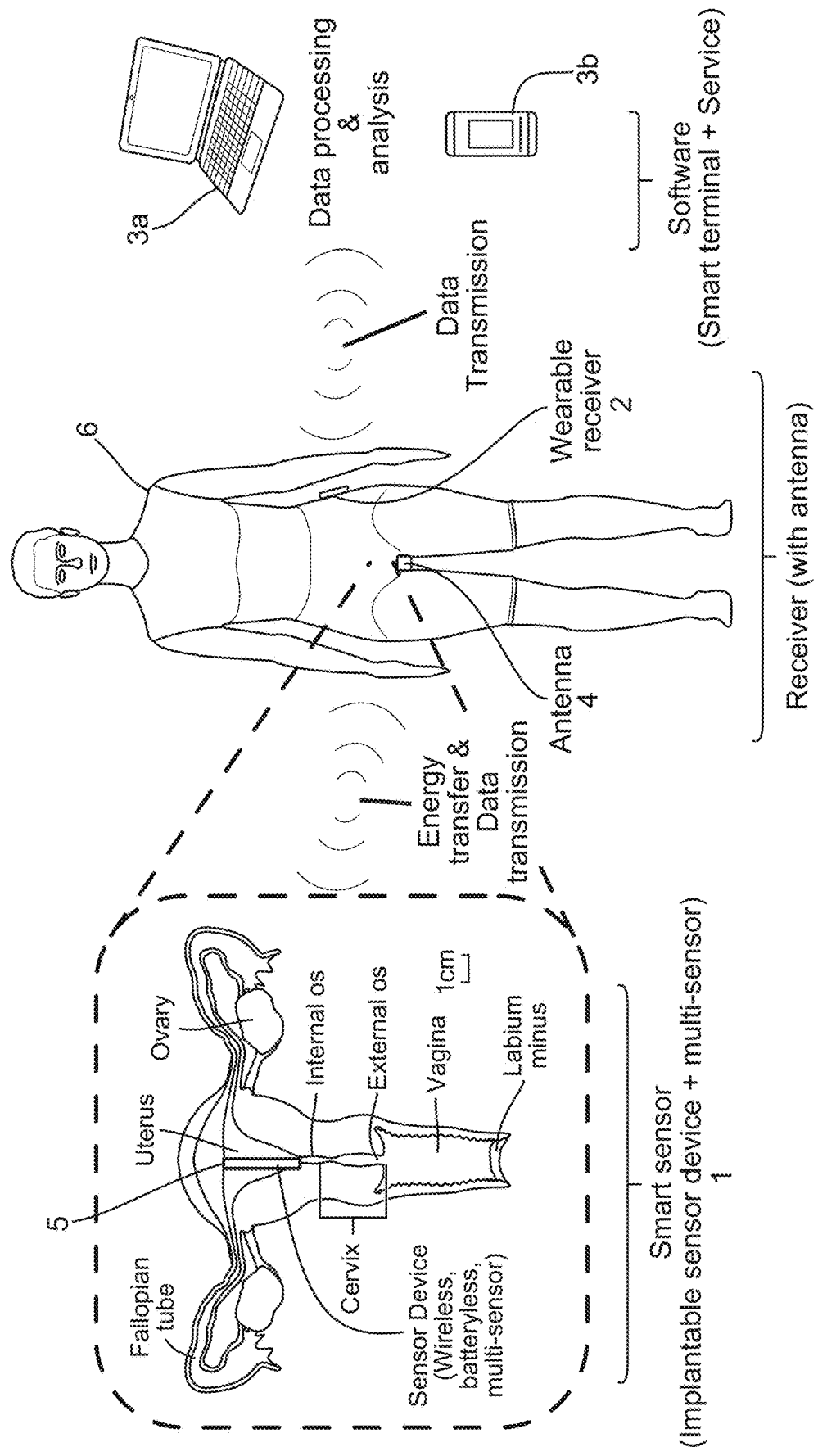
FIG. 1 schematically illustrates an intra-uterine monitoring system according to an embodiment of the invention.

Referring to FIG. 1, a three-module structured multi-parameter in-vivo sensing platform for intra-uterine environment monitoring is shown. The platform comprises a smart sensor 1 (implantable sensor device, which is suitably shaped and dimensioned for implantation in a human uterus), an external, generally wearable, receiver 2 and monitoring software installed on suitable data processing hardware, such as a computer 3a or portable electronic device 3b. The smart sensor 1 is a fully implantable (within the uterus 5 of a human female body 6) sensor device incorporating multiple embedded biosensors (intended for measuring temperature, dissolved oxygen concentration (DOC) and pH). Temperature, DOC and pH are considered to be the three most important parameters to measure for this application because they maintain a homeostatic controlled balance of gases and acid-base which is vital to human life and reproduction. They are likely to determine the receptivity of the intra-uterine environment to an implanting embryo.

The smart sensor 1 is capable of wirelessly receiving power from and wirelessly transmitting data to the wearable receiver 2 which is located outside the body of a user, and worn by the user. As a result, the smart sensor 1 dispenses with the need for a battery and cables, and is of comparable size to the widely-used IUDs (intra-uterine devices) for contraception. This is important, because for implantation in the uterus, a device must meet strict size limits. Compared with intra-uterine devices (IUDs) widely used for contraception, battery-based sensors have been found to be too large to be used in the uterus. Moreover, designs based on a battery typically have limitations due to the physical size of the battery and short lifetime before the battery is too depleted to continue operating. Furthermore, there are potential risks from the toxic material of battery.

The receiver 2 serves as a medium between the implantable sensor device 1 and the external data processing device running suitable software (and thus operating as a data analyser). In particular, the receiver 2 delivers energy to the sensor device and collects real-time information. An antenna 4 of the receiver 2 can be embedded into clothing and wired to the receiver 2. The software module is developed for in-vivo data uploading simultaneously to smart terminals or PC servers for post data processing and analysis. The software module consists of a set of monitoring software running on a PC or smart terminal which is designed to be a friendly user interface for data processing and system configuration. The positioning of the smart sensor 1 within the uterus is shown in FIG. 1. In particular, the smart sensor 1, which may typically have a generally elongate structure, is positioned substantially upright (vertical) within the uterus. As a result, the longitudinal axis of the smart sensor 1 is substantially vertical when the user is standing.

In this three-module structured system, the effectiveness of the wireless energy transfer and data communication between the smart sensor 1 and receiver 2 directly affect the usability of the intended system. An optimised design may not only result in better performance, smaller size, low power consumption and lower cost, but also improve end-user experience and clinical practise.

Figure 2:
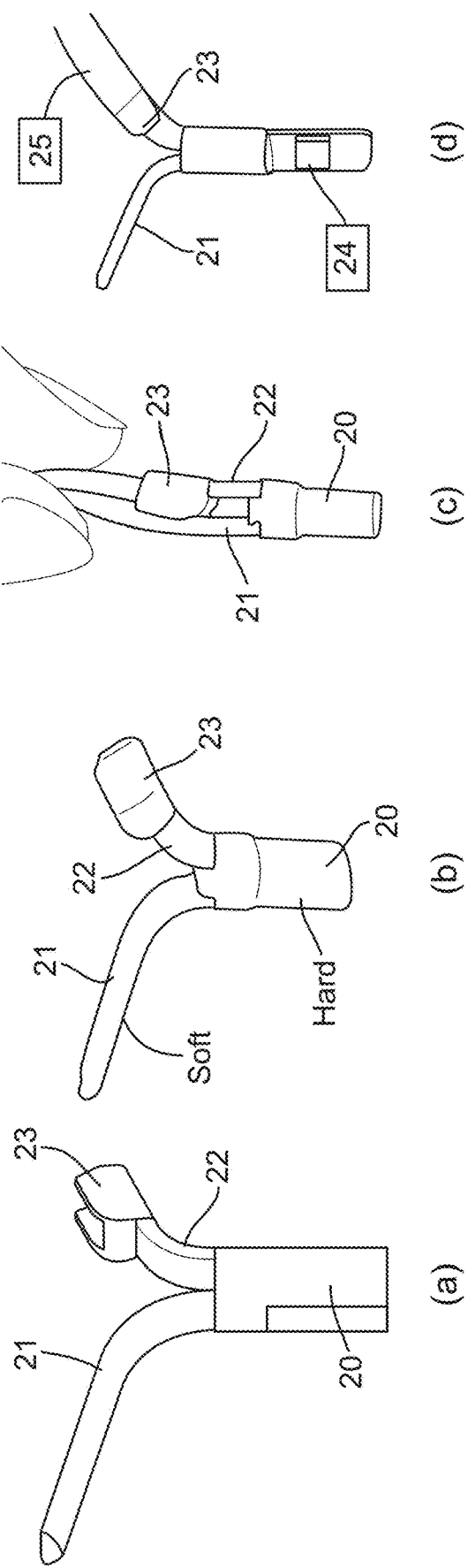
FIG. 2 schematically illustrates an implantable sensor device according to one embodiment.

Referring to FIG. 2, an example structure for the smart sensor 1 is shown. In FIG. 2(a), an upper portion of a T-type smart sensor can be seen to comprise a middle connector 20, a first arm 21, and a second arm 22 having a connector 23. In FIG. 2(b), it is explained that the middle connector 20 is formed of a different material with a different hardness than the first arm 21 and joint of the second arm 22. In particular, a relatively hard material is used for the main body and the connector 23, whereas a relatively soft material is used to form the first arm 21 and the joint on the second arm 22. From FIG. 2(c) is it shown how the first and second arms 21, 22 are bent together during delivery into the uterus and removal to aid insertion/removal. Once inserted, the first and second arms 21, 22 help to retain the smart sense 1 in place within the uterus. While in the present embodiment two arms are used, it should be understood that in other embodiments a single arm could be used, or more than two arms could be used. In FIG. 2(d), it can be seen that a main circuit board 24 is connected to the middle connector 20 and an antenna is fixed on the second arm 22 via the connector 23. The main circuit board 24 carries the sensors and the circuitry which will be described in detail below. In this arrangement, one of the arms serves both to help keep the smart sensor 1 in place within the uterus, and also serves as the antenna for communicating with (and receiving power from) the receiver 2. In the FIG. 2 smart sensor, the antenna is generally horizontal within the uterus, making it suitable for use with a receiver having an antenna embedded in upper garments. In alternative embodiments the antenna may not form part of an arm, but may be provided elsewhere.

Figure 3:
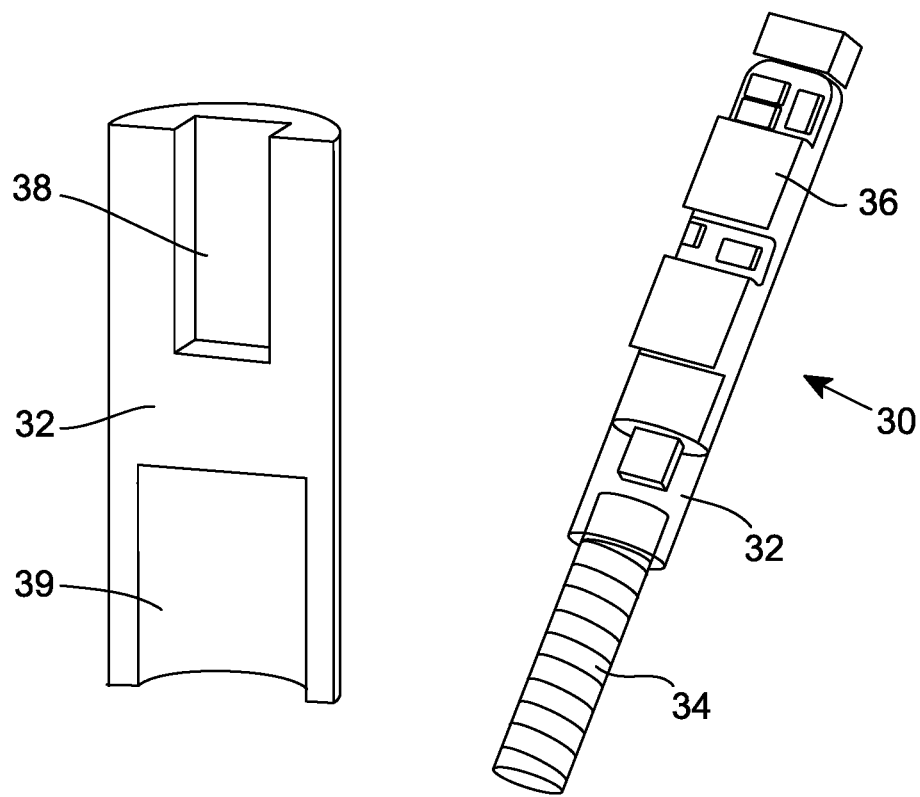
FIG. 3 schematically illustrates an implantable sensor device according to another embodiment.

Referring to FIG. 3, a simplified structure for the smart sensor is shown. The left hand side of FIG. 3 shows a cross section of a middle connector 32 and the right hand side of FIG. 3 shows a full smart sensor 30 including the internal connection of the middle connector 32. The middle connector 32 has two sockets, present here as a rectangular slot 38 for connection to a main circuit board 36 (with sensors and circuitry on board), and a circular slot 39 for connection to a tube antenna 34. The sensor device orientation of FIG. 3 is vertical in the uterus, making it suitable for use with a receiver having a belt antenna or an antenna embedded in underwear (or a disposable sanitary towel). It will be appreciated that the sensor device of FIG. 3 could be provided with one or more arms to assist with stabilising its position within the uterus if desired. Compared with other antenna types, a tube antenna can achieve a relatively small size and tight wind on a ferrite core because it does not require a coil frame. Considering fabrication complexity and the need for the sensor to be as small as possible, a tube antenna with a ferrite core is deemed as a particularly suitable antenna for the implantable sensor device.

Figure 4:
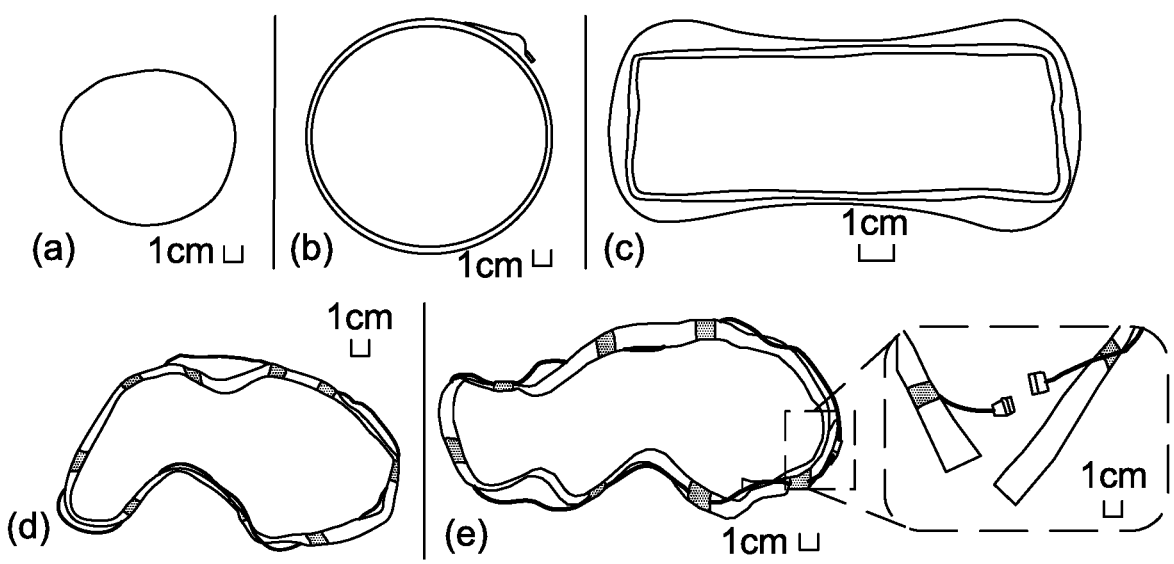
FIG. 4 schematically illustrates various possible implementations of a wearable antenna.

Referring to FIG. 4, various options for providing a receiver antenna in a wearable, or other, form are shown. In FIG. 4(a) an antenna is shown to be sealed in laminating paper and is able to be embedded into cloth, making it suitable for application to clothing such as underwear. In FIG. 4(b), a rigid antenna is shown formed on a plastic frame. Such an antenna could be usefully embedded into an item of furniture such as a chair or bed, permitting sensor data to be obtained from an implanted sensor while the subject is sitting or sleeping. In FIG. 4(c), an antenna is shown embedded in a disposable sanitary towel. In FIG. 4(d), an elastic antenna with a coil embedded on an elastic band is shown. This may form an elasticated belt as a continuous loop for a user to wear around their waist. In FIG. 4(e), a belt antenna includes a coil embedded in an elastic band with a multi-pin connector, or buckle, (to form a complete circuit when connected) and a row of hooks designed to make the belt adjustable. It will be appreciated that both the devices of FIGS. 4(d) and 4(e) may be worn as belts, and they each have their own advantages and disadvantages. The elasticated belt of FIG. 4(d) is smaller, with no bulky buckle, but needs to be put on over the feet/legs or chest/arms. The buckled belt of FIG. 4(d) is more like a normal belt, and may be made to fit the body more comfortably.

Figure 5:
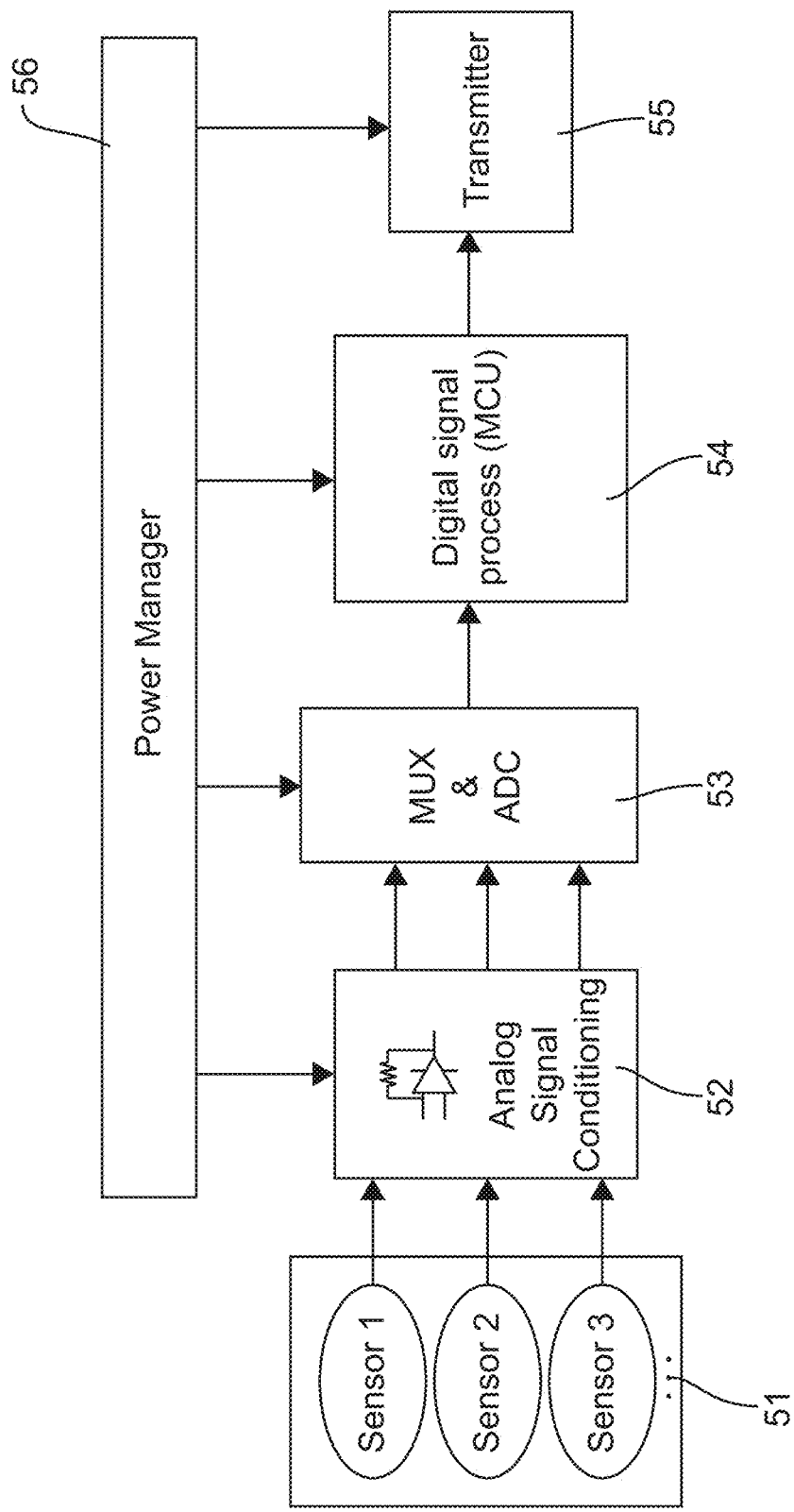
FIG. 5 is a schematic block diagram of an implantable sensor device.

Referring to FIG. 5, a block diagram of a suitable microsystem structure for the smart sensor is shown. To achieve data capture, signal processing and wireless communication, the microsystem includes integrated sensors or a multi-sensor array 51, an analogue signal conditioning circuit 52, an analogue to digital converter (ADC) 53 optionally including a multiplexer (MUX), a digital signal processor 54 or micro-programmed control unit (MCU), a wireless transmitter 55 and a power manager 56. In operation, the sensors 51 convert physical parameters into electronic signals. Sensors can be fabricated on tiny silicon chips based on microfabrication technologies which are suitable for microsystems. The conditioning circuit 52 is used to improve the quality of the analogue signals from the sensors 51. Generally, high end conditioning performance requires more complex circuits. A simpler conditioning circuit results in limited performance that requires further data processing after analogue-digital conversion. Therefore, a balance between signal conditioning performance and circuit complexity should be considered for the system implementation. A multiplexer (MUX) may be employed for circuit hardware sharing, which has the advantage of reducing device size and power consumption. The processer 54 undertakes logic control and digital signal processing. A micro-programmed control unit (MCU) is a widely-used component for flexible functionality and good scalability. At the same time, compared with a powerful processor, an MCU enables power consumption to be reduced. The wireless transmitter 55 and power manager 56 are provided for data transmission and power control respectively. Integration of these different units can facilitate device miniaturisation.

Figure 6:
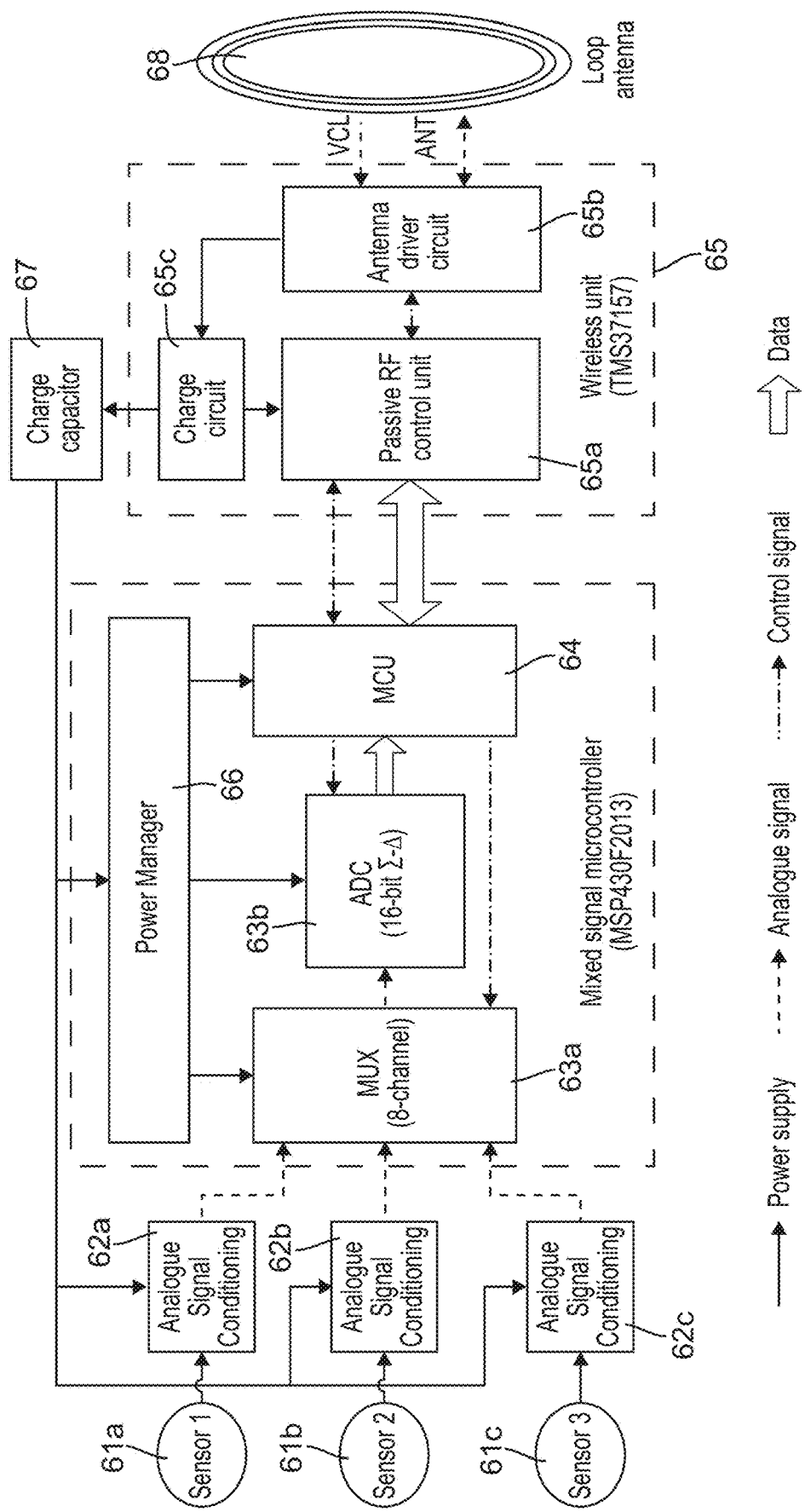
FIG. 6 is a more detailed schematic block diagram of an implantable sensor device.

Referring to FIG. 6, the main structure of the sensor device is shown in greater detail, including sensors 61*a*, 61*b*, 61*c* (temperature, DOC and pH in this case), respective analogue signal conditioning units 62*a*, 62*b*, 62*c* (one for conditioning the output of each of the sensors 61*a*, 61*b*, 61*c*), a multiplexer 63*a* (to allow an array of sensors to be interfaced with the ADC), analogue to digital converter 63*b* and MCU 64, and a transmitter 65. Two-way communication with the MCU from outside the body is also possible, for example to wake it from a power saving sleep-state. Furthermore, the antenna can be used for wireless power transfer through inductive coupling. The transmitter 65 here comprises a passive RF control unit 65*a* for communicating with the MCU 64, and controlling an antenna driver circuit 65*b* and a charging circuit 65*c*. The antenna driver circuit is capable of bidirectional data communication with the external receiver (Antenna, ANT) via an antenna (in this case a loop antenna) 68, as well as receiving power (charging voltage, VCL) via the antenna 68. It will therefore be understood that the system utilises wireless power transfer through inductive coupling, using a low frequency RFID signal to transmit data and receive power through the abdominal region of a user. The charge circuit 65*c* is able to charge a capacitor 67 and also deliver power to the control unit 65*a* using the electrical power received via the antenna 68 and driver circuit 65*b*. All power is managed through the power management block 66. The flow of power around the circuitry of FIG. 6 is indicated by solid directional arrows. Analogue data signal flow is indicted by a first type of dashed directional arrow. Control signal flow is indicated by a second type of dashed directional arrow. Data flow is indicated by solid block arrows. It can be seen that the charge capacitor 67 delivers electrical power to the power manager 66 (which in turn manages power delivery to the multiplexer 63*a*, the ADC 63*b* and the MCU 64), as well as to the signal conditioning units 62*a*, 62*b*, 62*c*. The capacitor 67 is preferably a ceramic capacitor. This type of capacitor is particularly suitable for the present purposes for safety reasons, for example because it does not utilise toxic materials and has little or no risk of leakage.

Figure 7:
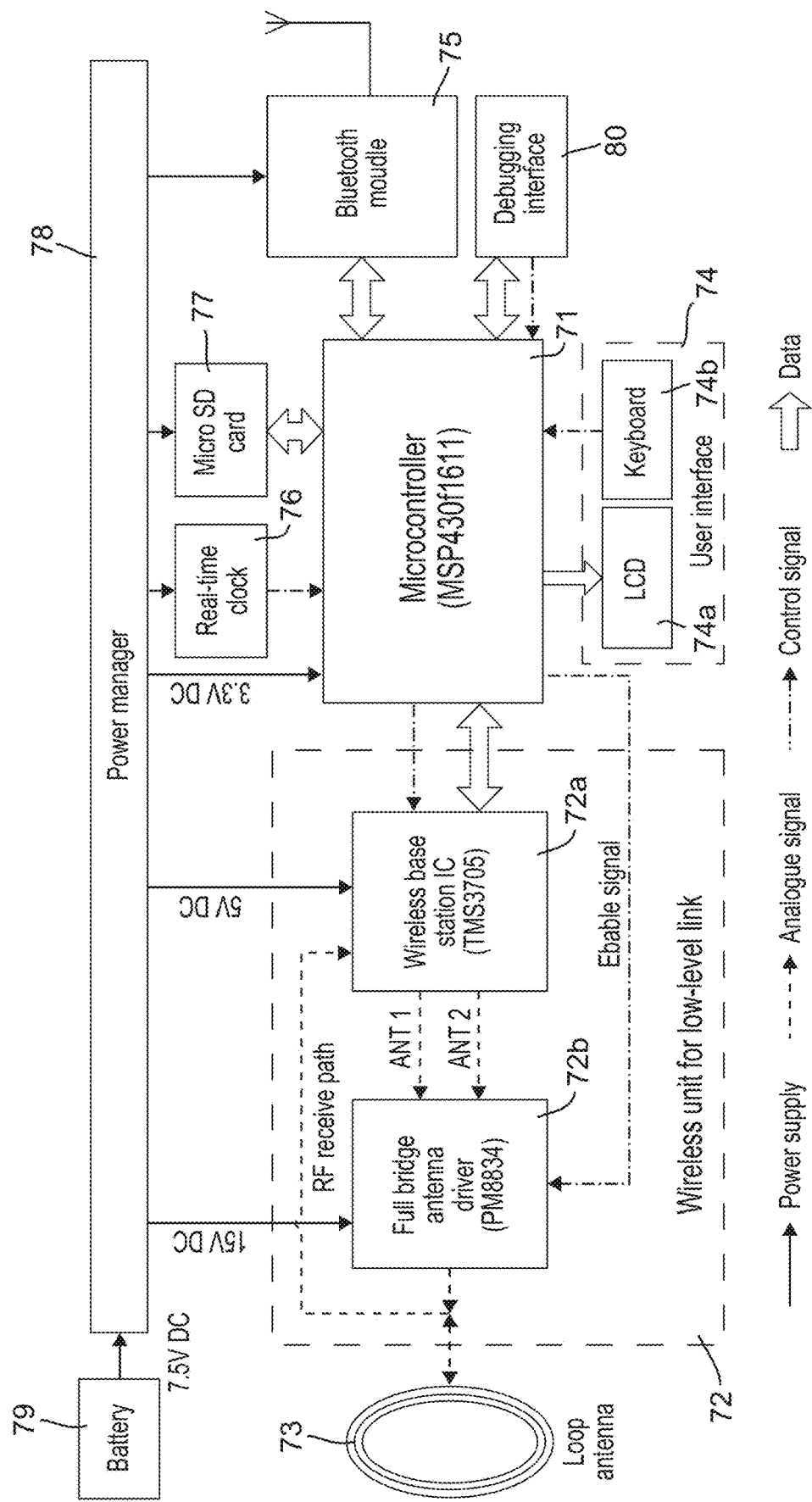
FIG. 7 is a schematic block diagram of a wearable receiver device.

Referring to FIG. 7, an overview of the receiver structure is shown. A microcontroller 71 links and controls different peripherals. A low-level wireless unit 72 provides wireless energy transfer to and data communication with the implantable sensor device via a loop antenna 73. The wireless unit 72 comprises a wireless base station integrated circuit 72*a* for implementing an RF analogue front end to generate the antenna driving signal, and to modulate and demodulate the digital signal, and a full bridge antenna driver 72*b* for providing the output power and driving the antenna. A user interface 74 comprising an LCD display 74*a* and a keyboard 74*b* is able to display received sensor data and system information provided by the microcontroller 71, and to offer a facility for a user to operate the device, again via the microcontroller 71. A Bluetooth module 75 provides high-level communication with servers or smart terminals, where data analysis can be performed. A real-time clock 76 provides time information, for example to give a time stamp to each data item, and to achieve continuous measurement, and a micro SD card interface 77 provides local data storage. A power manager 78 converts a power supply from a rechargeable battery 79 to match the different voltage requirement of the peripherals. The flow of power around the circuitry of FIG. 6 is indicated by solid directional arrows. Analogue data signal flow is indicted by a first type of dashed directional arrow. Control signal flow is indicated by a second type of dashed directional arrow. Data flow is indicated by solid block arrows.

Figure 8:
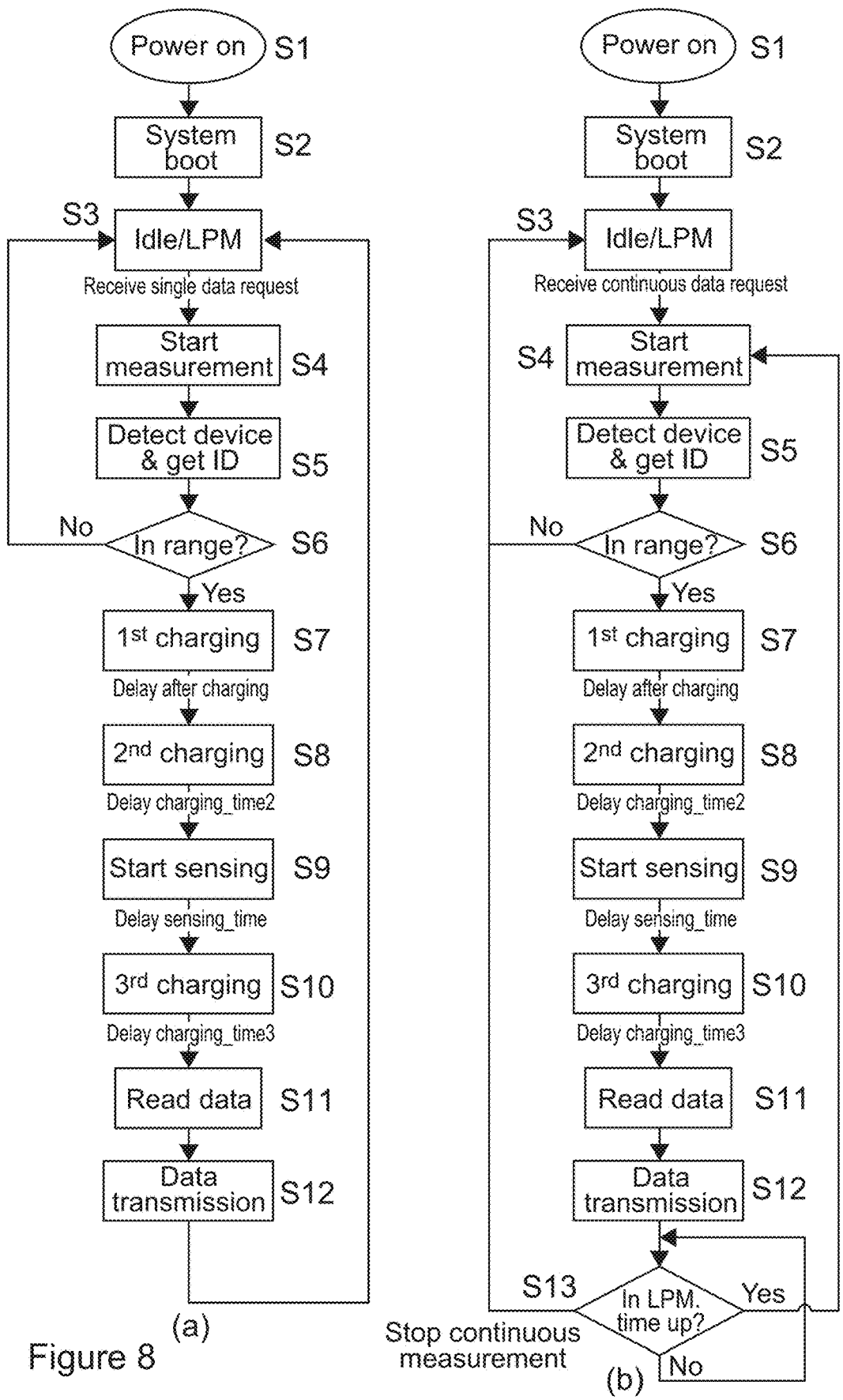
FIG. 8 is a schematic flow diagram of the operation of the implantable sensor device.
Figure 8:
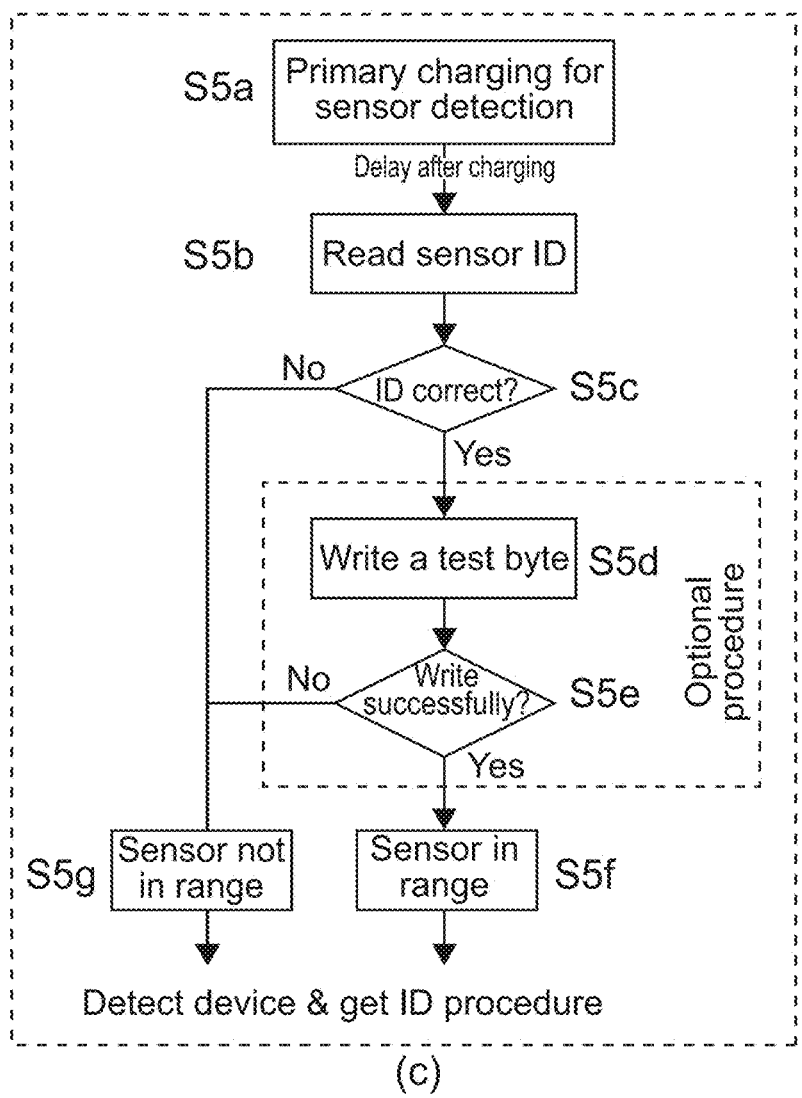
Figure 8:
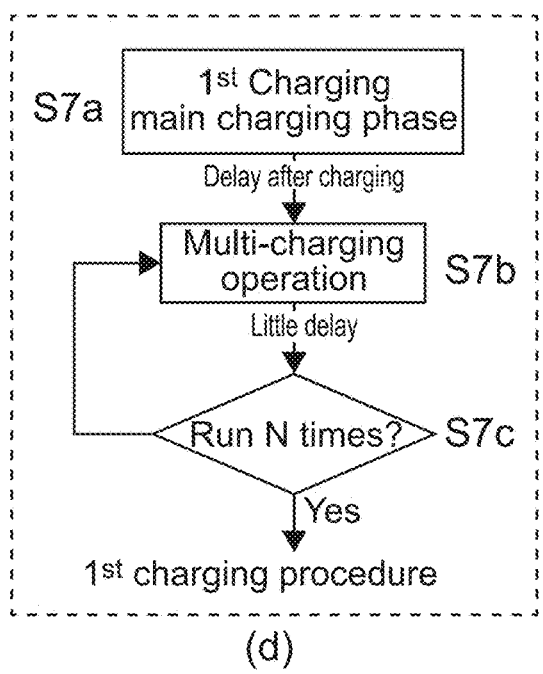

Referring to FIG. 8, flow charts of operating procedures for single sampling (a) and continuous sampling (b) are shown. For single sampling, at a step S1 the system is powered on, and then boots at a step S2, initialising the various circuitry shown in FIG. 7. After this, the system enters an idle or lower power mode at a step S3, which it remains in until it receives a single data request (for example in response to a user actuating the wearable receiver or a wirelessly connected control device. In response to such a trigger, at a step S4 a sampling/measurement cycle is initiated. At a step S5, the receiver attempts to detect the smart sensor device and obtain its identifier. This procedure is described in more detail in FIG. 8(*c*). If at a step S6 it is determined that the sensor device is not in range and cannot be detected, then the process returns to the idle/lower power state S3. If at the step S6 the sensor device is found to be in range, then at a step S7 a first charging operation is conducted. The first charging operation is described in more detail in FIG. 8(*d*). The first charging operation is intended to provide the sensor device with sufficient power to carry out a boot procedure in which the circuitry of FIG. 6 is powered up and initialised. More specifically, the booting procedure may include hardware initialisation, MCU state initialisation, working parameter initialisation (firmware) and entering the low-power mode immediately after the booting, pending instructions to start operation. It will be appreciated that the boot procedure will use some or all of the power provided in the first charging operation. The step S7 is followed, after a short delay (during which the sensor device will be booting up) by a second charging operation at a step S8, which replenishes the charge in the capacitor of the sensor device, whereupon the sensor device is able to start sensing (but not transmitting) at a step S9. At a step S10, a third charging operation is used to transfer enough energy to the sensor device for data to be read from the sensors at a step S11, and for wireless data transmission of the sensor data to take place at a step S12. After data transmission, the system returns to the idle mode at the step S3 and waits for a next sampling cycle. The procedure for continuous sampling (b) is similar to a single sampling cycle, and corresponding steps are labelled using the same step numbers. The difference here is that the sampling cycle runs automatically at pre-set time intervals, governed by a step S13, which is able to either keep the system idle or in the low power mode, cancel the task or trigger the start of the operation by returning the process to the step S4. In effect, after data transmission at the step S12, the system enters a sleep mode and a timer counts down to trigger the next sampling cycle. If a "Cancel" button is triggered, the system would return back to the idle mode. This procedure serves to transfer energy efficiently, limit crosstalk noise between energy transfer and data transmission due to the shared link and shorten the sampling cycle. Multi-step charging is adopted for the sensor device rather than single charging, as it ensures sufficient energy for each working step and less overall charging time than single charging.

Referring to FIG. 8(c), the detect device and obtain ID procedure (step S5) is described in greater detail. In particular, at a step S5a, a primary charging operation for sensor device detection is carried out. This need only charge part of the sensor device, for example the wireless unit 65, which is sufficient for the sensor ID to be read at a step S5b, a short time after the charging step S5a has taken place. At a step S5c it is determined whether the read ID is correct. If not (for example the ID is unrecognised, or corrupted due to a poor wireless connection), then at a step S5g a signal is generated (for use by the step S6) indicating that the sensor device is not in range. If however the ID is determined to have been read correctly at the step S5c, then a test byte is written to the sensor device at a step S5d. It is then determined at a step S5e whether the writing of the test byte has been successful. If not, then again, a not in range signal is generated at the step S5g. If however the test byte is determined to have been written successfully, then at a step S5f a signal is generated (for use by the step S6) indicating that the sensor device is in range. The test write procedure of the step s5d and S5e is an optional procedure for confirming the reliability of the wireless connection between the sensor device and the receiver.

Referring to 8(d), the first charging procedure of the step S7 is described in more detail. In particular, at a step S7a a first charging main charging phase is carried out. This is a single, continuous charging phase in which power is delivered to the sensor device to charge the capacitor. The main charging phase may for example charge the capacitor to 50% of capacity relatively quickly. However, continuous charging beyond this may cause excess heating of the sensor device or components thereof. Accordingly, the step S7a is followed by multiple iterations of steps S7b (which transfers a small amount of power to the sensor device) and S7c (which cycles back to the step S7b until it has been carried out N times). The combinations of the steps S7a, S7b and S7c fully charge the capacitor. The use of multiple short charges controls the heating effect by limiting the continuous generation of heat at the coil and power driver circuit (on the wearable receiver), and for the implantable sensor inhibits overheating on the coil.

The low power state may be a "sleep" state in which the device is substantially powered down to conserve power, but is capable of being woken up to operate. In contrast, the idle state may be an operational state in which the device is merely awaiting an instruction. The device may be quicker to react when in the idle state than in the lower power (sleep) state.

Figure 9:
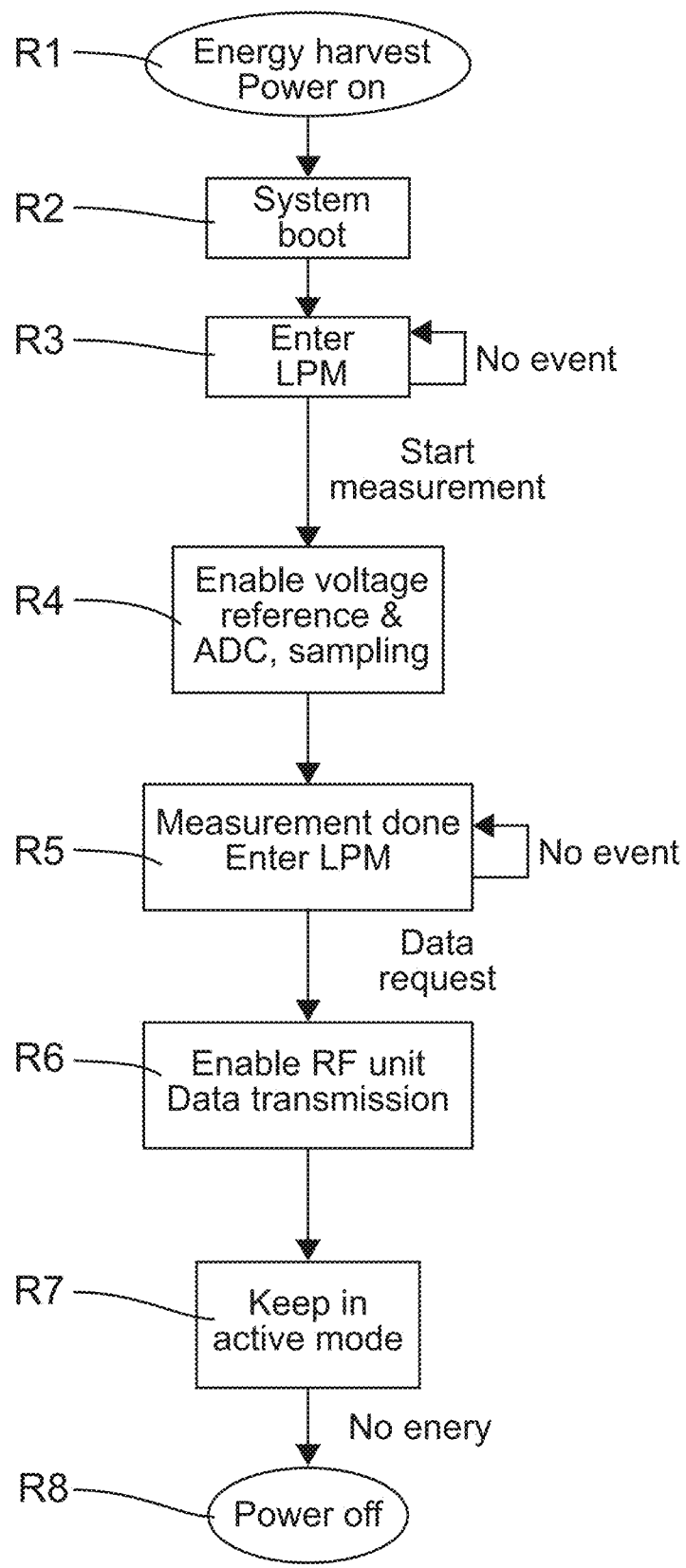
FIG. 9 is a schematic flow diagram of a multi-charging based operation of the monitoring system.

Referring to FIG. 9, a flow chart of the operation of the implantable sensor device is shown. FIG. 9 sets out the operation of the sensor device following its detection at the steps S5 and S6 of FIG. 8. At a step R1, energy is harvested at the sensor device by virtue of the step S7 (first charging procedure) and is used to power on the sensor device and perform a system boot at a step R2, as discussed above. At a step R3, the sensor device enters a low power mode, which continues while no events occur. If the sensor device receives an instruction to start measurement from the receiver device, then at a step R4 the sensor device enables a voltage reference and the analogue to digital converter circuitry, and start taking measurements using the sensors. The step R4 is carried out using power provided to the sensor device at the second charging procedure at S8 of FIG. 8. Once the measurements have been made, and stored locally, the sensor device again enters the low power mode at a step R5, which again persists until interrupted by an instruction from the receiver device (data request), at which point the process moves on to a step R6, where the RF unit of the sensor device is enabled, and transmission of sensor data from the sensor device to the receiver device takes place. The step R6 is carried out using power provided to the sensor device at the third charging procedure at the step S10 of FIG. 8. Following the step R6, the sensor device then remains in the active mode at a step R7 until the capacitor is exhausted, at which point the sensor device powers off at a step R8. The reason for actively exhausting the capacitor is so that the sensor device is fully reinitialised each time it is used, and so that the capacitor can be energised consistently from its empty state to a full state using the charging steps indicated in FIG. 8.

Figure 10:
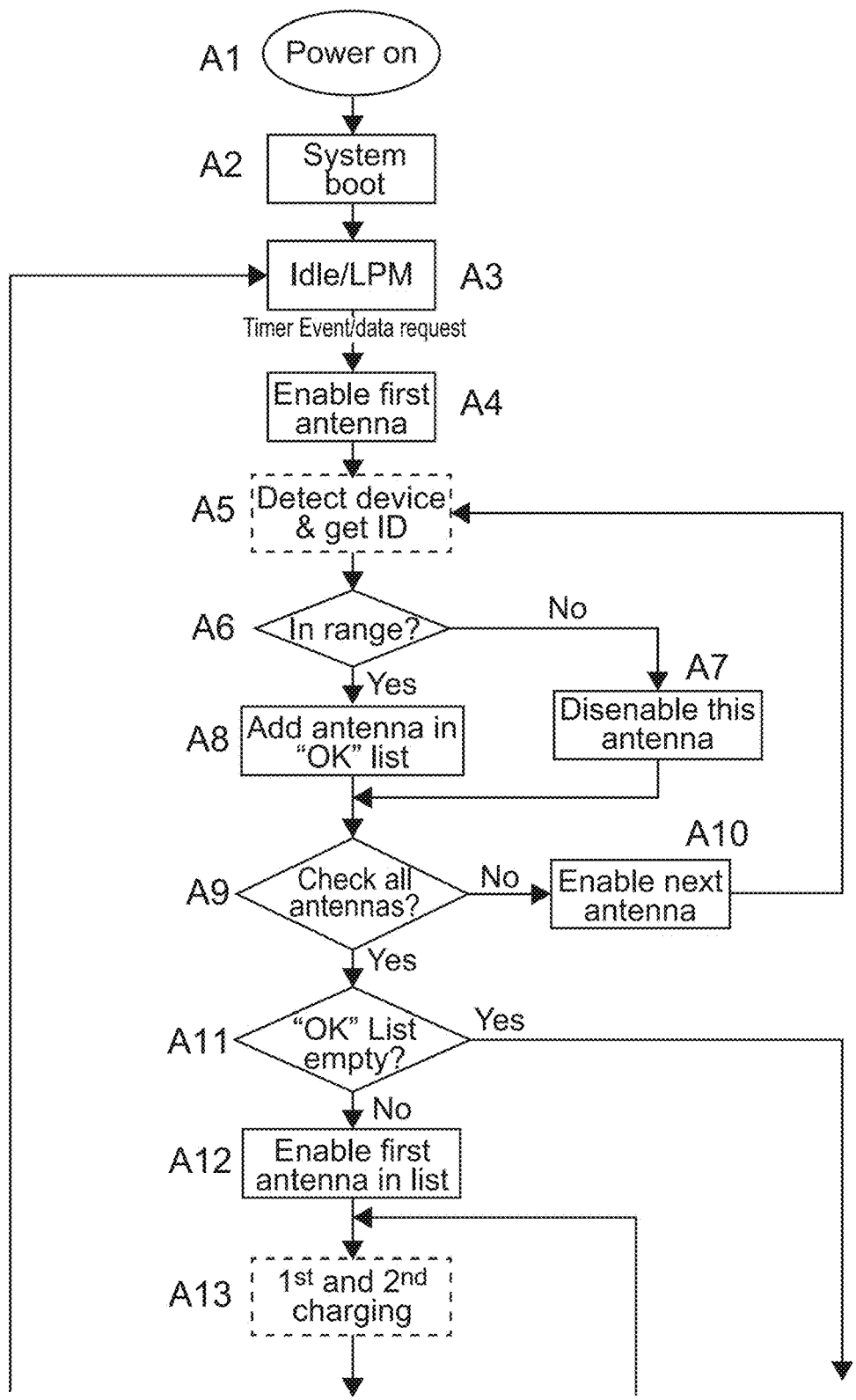
FIG. 10 is a schematic flow diagram of a multi-antenna procedure.
Figure 10:
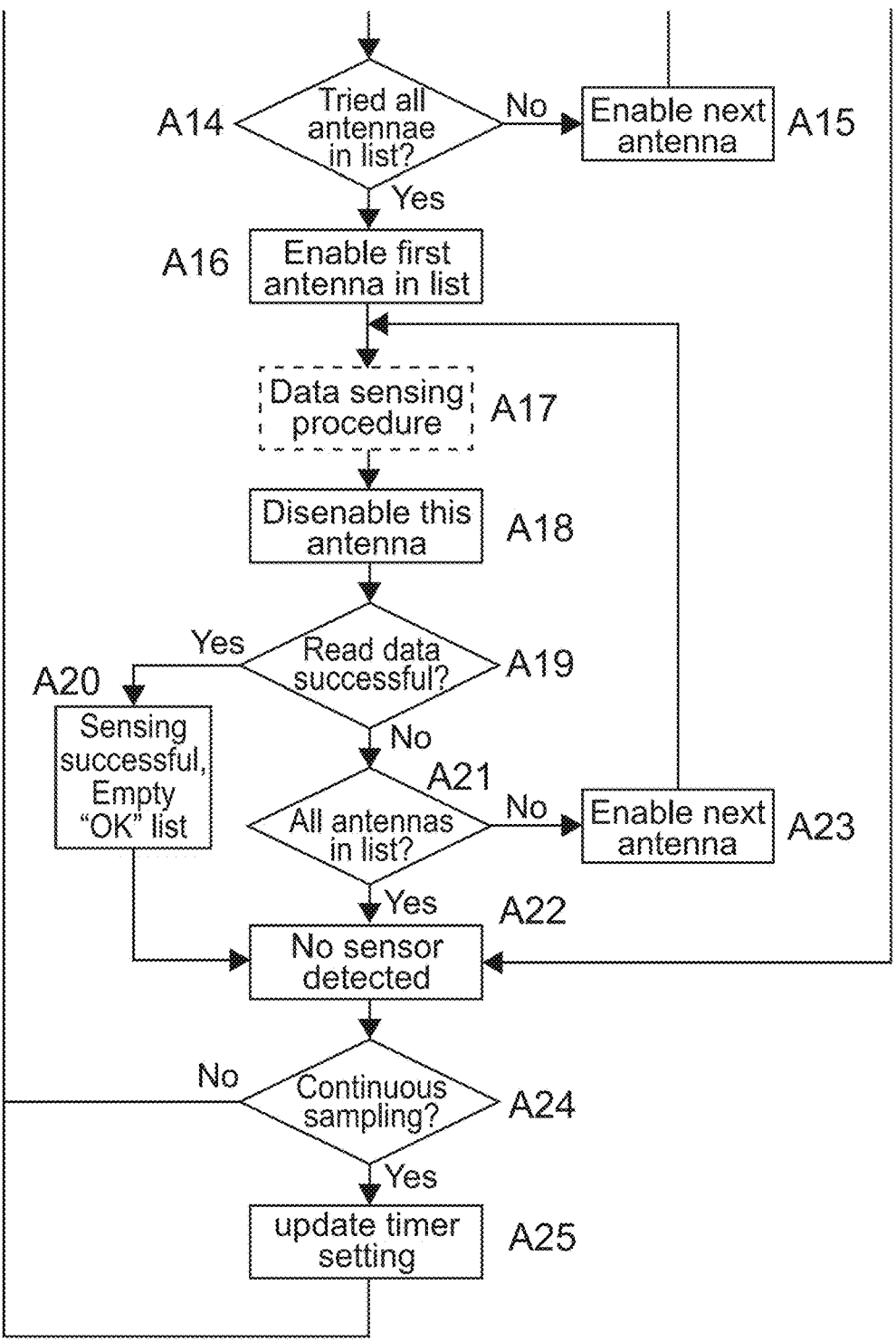
Figure 10:
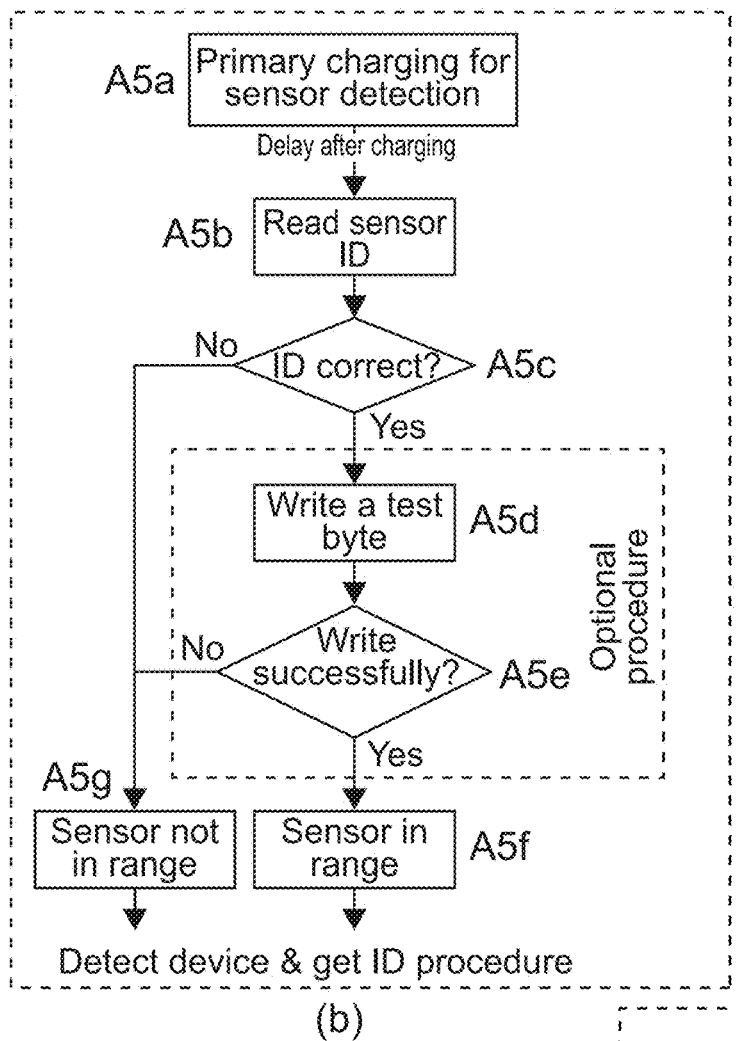
Figure 10:
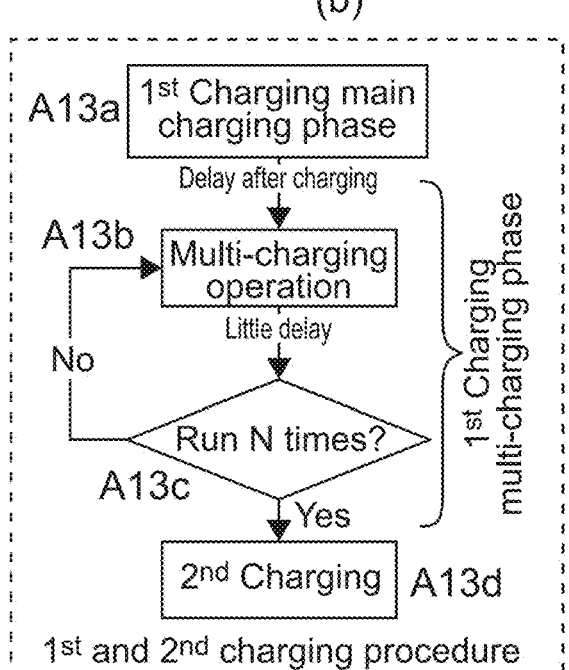
Figure 10:
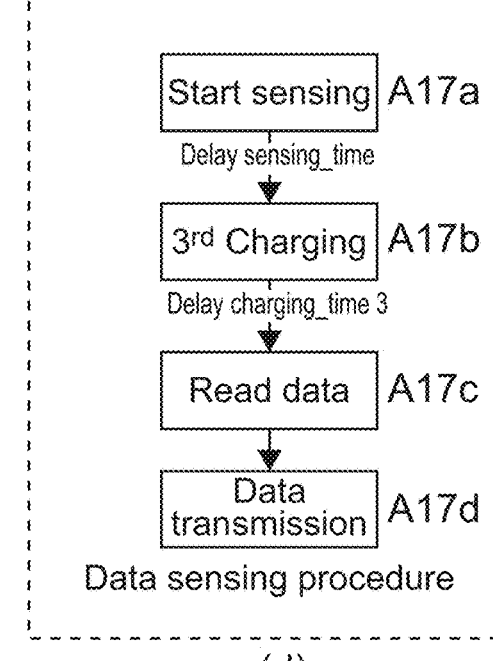

Referring to FIG. 10, flow charts of operating procedures for a multi-antenna receiver system are shown. The multiple antennae could be present in a single device, such as a wearable receiver, or a receiver utilising an antenna embedded within an item of furniture, or alternatively one (or more) antennae could be provided in a wearable form, while another one (or more) could be embedded in an item of furniture. As will be understood from the following description, the plural antennae work cooperatively to improve overall performance. Compared to a single receiver system, a challenge for a multi-antenna receiver system is how to coordinate the different antennas and perform sampling quickly and efficiently, irrespective of the position and orientation of the sensor device with respect to the various antennae. In FIG. 10(a), a working procedure for a multi-antenna receiver system is explained. At a step A1, the system is powered up. At a step A2, the system is booted in the same manner as the step S2 of FIG. 8. The system then enters an idle mode or low power mode at a step A3 and waits for an event trigger, such as a button being pressed, or a timer event in the case of continuous sampling. Once triggered, a sampling (measurement) cycle is started. To achieve this in a multi-array setup, at a step A4, a first antenna is enabled, and at a step A5 an attempt is made to detect the sensor device and obtain its identifier. This process is set out in FIG. 10(b), which corresponds precisely to FIG. 8(b). In particular, the steps A5a to A5g of FIG. 10(b) are the same as the steps S5a to S5g, and will not be described again. If it is determined at a step A6 that the sensor device is not in range of that antenna, then at a step A7 the first antenna is disabled. If it is determined at the step A6 that the sensor device is in range of the first antenna, then this antenna is added to an "OK" list (a list of available antennas) at a step A8. Then, at a step A9 it is determined if all antennas have been checked. If not, then at a step A10 the next antenna is enabled, and the process returns to the step A5, where the steps A5 to A8 will be repeated for the next antenna. This process continues until all antennae have been considered and either added to the "OK" list or disabled. After cycling through all antennas, at a step A11 it is determined if the "OK" list is empty. If so, then it is determined at a step A21 that no device is detected. Otherwise, the process moves onto a step A12, where the first antenna in the "OK" list is enabled. In particular, at a step A13 first and second charging procedures are carried out by the first antenna (as will be discussed in FIG. 10(c)). At a step A14 it is determined if all antennae in the list have carried out the charge procedures. If not, then at a step A15 the next antenna in the list is enables and the steps A13 and A14 are repeated. When at the step A14 it is determined that all antennae in the list have carried out the charge procedures, then at a step A16 the first antenna in the "OK" list is selected, and triggers the data sensing procedure discussed above in relation to FIG. 8 at a step A17 (see also FIG. 10(d)). This antenna is then disabled at a step A18. It is then determined at a step A19 whether the reading of the sensor data has been successful. If so, then it is not necessary to utilise any of the other antennae in the "OK" list, and the list can be emptied at a step A20. Otherwise, if the reading of the sensor data has not been successful then at a step A21 it is determined if all antennae have attempted to obtain sensor data from the sensor device. If so, then the process progresses to the step A22 where it is determined that no device is detected (or at least that no device can be read). Otherwise, at a step A22 the next antennae device in the "OK" list is selected, and the steps A17 to A22 are repeated for the next antennae device. Following the step A22, it is determined at a step A23 whether the continuous sampling mode is active. If not, then the process returns to the idle state at the step A3. If the continuous sampling mode is active, then a timer is set at a step A24 and the process then returns to the idle mode or low power mode at the step A3. Following the expiry of the timer, the step A4 will commence. In this way, it will be appreciated that the charging phase of all available antennae entered in the "OK" list is carried out. The charging by all available antennas (one by one) enables sufficient energy to be delivered to the device, even when the position and orientation of each individual antenna of the receiver were not optimal. Subsequently, the available antennas read the data successively after the charging phase. Once the data has been retrieved successfully, this sampling cycle is finished. If all available antennas do not get any correct data, then a failed message may be sent back to the software.

Turning to FIG. 10(c) a multi-charge procedure is shown to comprise a first charging step A13a, followed by a multi-charging operation executed N times represented by the steps A13b and A13c, followed by a second charging step A13d. Turning to FIG. 10(d), a data sensing procedure is shown in which the sensor device is instructed to start sensing at a step A17a, and then the sensor device is charged (by the receiver device) at a step A17b in order to provide sufficient power for a step A17c of reading the sensor data and a step A17d of transmitting the read sensor data to the receiver device.

As discussed above, electromagnetic induction wireless transmission technology is used for near field energy transfer through the use of two coupled coils, primary and secondary coils, provided at the receiver device and implantable sensor respectively. The electric current flowing through the primary coil creates a magnetic field that acts on the secondary coil producing an induced current within it. Tight coupling is needed for high energy harvest efficiency and long working distance. Increasing the distance between the coils results in the magnetic field extending beyond the secondary coil receiving area and leads to a loss of transmitted energy. Within the intended application, an implantable sensor device requires small size, low power consumption and a relatively short working distance of around 10 cms. Energy loss due to tissue absorption of the wireless signals (the electromagnetic energy is transformed to other forms of energy by matter within the medium of tissues, for example, to heat) is dependent on the signal frequency. Signals at lower frequencies have better propagation characteristics and result in less tissue absorption. Therefore, wireless energy transfer based on electromagnetic induction at low frequency is employed for the implantable sensor device. The circuit for wireless energy transfer can also serve as the wireless data communication as a low frequency RFID link, reducing the need for additional circuits or board space for data communication. In the intended application, the in-vivo information and system configuration do not require high data rate transmission and the LF RFID link can provide sufficient data bandwidth to meet the demand. The data communication range is usually further than the energy transfer distance meaning it is not the bottleneck of the effective working distance.

While the various techniques, and the implantable sensor device and external receiver have been explained in the context of intra-uterine monitoring, it will be understood that these techniques and structures could be applied to other body-cavity monitoring, such as within a vagina, bladder or digestive tract of a human or animal body.

The invention claimed is:

1. An intra-uterine monitoring system comprising:
   an implantable sensor device, shaped and dimensioned for implantation in a uterus for measuring conditions within the uterus to generate sensor data; and
   a wearable receiver device, for wirelessly receiving the sensor data generated by the implantable sensor device, wherein the wearable receiver device is operable to wirelessly charge the implantable sensor device, and
   wherein the wearable receiver device provides electrical power to the implantable sensor device in a plurality of charging periods over a single cycle of operation.

2. An intra-uterine monitoring system according to claim 1, wherein the wearable receiver device comprises an antenna, transceiver circuitry and a power source, and the implantable sensor device comprises an antenna, a charging circuit and a controller, wherein the wearable receiver device is operable to transmit electrical power from the antenna of the wearable receiver device to the antenna of the implantable sensor device via electromagnetic coupling, the electrical power being used by the charging circuit to store electrical power for operating the sensors of the implantable sensor device and for transmitting sensor data to the wearable receiver device.

3. An intra-uterine monitoring system according to claim 2, wherein the implantable sensor device comprises a capacitor, and the charging circuit stores the electrical power by charging the capacitor.

4. An intra-uterine monitoring system according to claim 2, wherein the power source is a rechargeable battery.

5. An intra-uterine monitoring system according to claim 1, wherein the plurality of charging periods comprises a first charging period for providing the implantable sensor device with electrical power to support the operation of the sensors in acquiring sensor data and a second charging period for providing the implantable sensor device with electrical power to support the transmission of the acquired sensor data to the wearable receiver device.

6. An intra-uterine monitoring system according to claim 5, wherein the plurality of charging periods comprising a third charging period, carried out before the first charging period, for providing the implantable sensor device with electrical power to support a booting procedure.

7. An intra-uterine monitoring system according to claim 6, wherein the third charging period comprises an initial charging operation and a variable length of time multi-charging operation.

8. An intra-uterine monitoring system according to claim 1, wherein the wearable receiver device comprises a plurality of antennae, each antenna being operable to wirelessly charge and receive data from the implantable sensor device.

9. An intra-uterine monitoring system according to claim 1, wherein the wearable receiver device comprises a first antenna and a second antenna is provided in an item of furniture, the first and second antenna together comprising a plurality of antennae.

10. An intra-uterine monitoring system comprising:
an implantable sensor device, shaped and dimensioned for implantation in a uterus for measuring conditions within the uterus to generate sensor data; and
a wearable receiver device, for wirelessly receiving the sensor data generated by the implantable sensor device,
wherein the wearable receiver device comprises a plurality of antennae, each antenna being operable to wirelessly charge and receive data from the implantable sensor device, and
wherein the wearable receiver device comprises a controller, the controller being operable to sequentially charge the implantable sensor device using a plurality of the antennae.

11. An intra-uterine monitoring system according to claim 10, wherein the controller is operable to identify which of the plurality of antennae are able to wirelessly detect the implantable sensor device prior to a charging operation, and to sequentially charge the implantable sensor device using each identified antenna.

12. An intra-uterine monitoring system according to claim 11, wherein the controller is operable to attempt to obtain the sensor data using one of the identified antenna, and if the attempt fails then attempts to obtain the sensor data using one or more other of the identified sensors.

13. An intra-uterine monitoring system according to claim 1, wherein the implantable sensor device comprises one or more of a temperature sensor, a pH sensor, and a dissolved oxygen sensor.

14. An intra-uterine monitoring system according to claim 1, wherein the implantable sensor device comprises one or both of an electrical conductivity sensor and a pressure sensor.

15. An intra-uterine monitoring system according to claim 1, wherein the implantable sensor device comprises a body and one or more arms, the arms projecting laterally from the body to secure the sensor within the uterus.

16. An intra-uterine monitoring system according to claim 15, wherein the implantable sensor device comprises a pair of arms positioned at or proximate one end of the body and extending generally away from each other.

17. An intra-uterine monitoring system according to claim 1, wherein the wearable receiver device is provided in a garment.

18. An intra-uterine monitoring system according to claim 17, wherein the garment is a belt to be worn around the waist of a user.

19. An intra-uterine monitoring system comprising:
an implantable sensor device, shaped and dimensioned for implantation in a uterus for measuring conditions within the uterus to generate sensor data; and
a wearable receiver device, for wirelessly receiving the sensor data generated by the implantable sensor device,
wherein the wearable receiver device is a sanitary pad.

20. An intra-uterine monitoring system according to claim 1, wherein the wearable receiver device comprises a transmitter for wirelessly transmitting received sensor data to an external device.

21. An intra-uterine monitoring system according to claim 20, wherein the external device is a portable electronic device or a computer.

22. A wearable receiver device, for wirelessly receiving sensor data generated by an implantable sensor device implanted in a uterus to measure conditions within the uterus, wherein the wearable receiver device comprises an antenna, transceiver circuitry and a power source, the wearable receiver device being operable to transmit electrical power from the power source via the antenna and transceiver circuitry of the wearable receiver device to the implantable sensor device to wirelessly charge the implantable sensor device, and wherein the wearable receiver device wirelessly provides electrical power to the implantable sensor device in a plurality of charging periods over a single cycle of operation.

* * * * *